United States Patent [19]

Smith

[11] 3,951,889

[45] Apr. 20, 1976

[54] FLUID ABSORBENT ALLOY FIBERS

[75] Inventor: Frederick R. Smith, Wilmington, Del.

[73] Assignee: FMC Corporation, Philadelphia, Pa.

[22] Filed: Dec. 6, 1974

[21] Appl. No.: 530,476

Related U.S. Application Data

[62] Division of Ser. No. 309,076, Nov. 24, 1972.

[52] U.S. Cl................................ 260/17 R; 128/284; 128/285; 260/9; 260/17.4 CL
[51] Int. Cl.$^2$.......................................... C08L 1/28
[58] Field of Search............... 260/17 R, 17.4 CL, 9; 106/165; 128/284, 285; 264/184, 186, 188, 189, 191, 194

[56] References Cited

UNITED STATES PATENTS

| | | | |
|---|---|---|---|
| 2,499,501 | 3/1950 | Hollihan | 264/194 |
| 3,146,116 | 8/1964 | Bates | 106/165 |
| 3,187,747 | 6/1965 | Burgeni | 128/285 |
| 3,318,990 | 5/1967 | Kajitani | 264/188 |
| 3,377,412 | 4/1968 | Franks | 260/17 |
| 3,509,249 | 4/1970 | Kuzmak | 264/188 |

FOREIGN PATENTS OR APPLICATIONS

| | | | |
|---|---|---|---|
| 6,506,343 | 12/1965 | Netherlands | 264/188 |

*Primary Examiner*—Harold D. Anderson
*Assistant Examiner*—Edward Woodberry

[57] ABSTRACT

Alloy fibers having high fluid-holding capacity being comprised of a matrix of non-derivatized regenerated cellulose having regenerated cyanoethyl cellulose and polyvinylpyrrolidone uniformly dispersed therein.

4 Claims, No Drawings

FLUID ABSORBENT ALLOY FIBERS

This application is a division of my application Ser. No. 309,076, filed Nov. 24, 1972.

The present invention is directed to alloy fibers having high fluid-holding capacity.

Known in the art are alloy fibers, consisting of sodium carboxymethyl cellulose and regenerated cellulose, which can be employed in various articles which are intended to absorb body liquids. While the fluid-holding capacity of these alloy fibers is greater than that of conventional regenerated cellulose fibers, this advantage is at least partially offset by their high manufacturing costs.

One mode of making such known alloy fibers involves the mixing of sodium carboxymethyl cellulose into viscose and then converting this mixture into fibers using the conventional viscose spinning system. Drying of the resulting alloy fibers to cardable form is difficult. This objective can be attained, however, by treating the alloy fibers with special finishes, removing water therefrom with alcohol, and then finally drying the alcohol-wet fibers. Aside from introducing greater complexity into the manufacturing process, the finishing and drying of the alloy fibers by solvent exchange is a relatively costly procedure. Accordingly, a primary object is to provide new or generally improved and more satisfactory absorbent alloy fibers.

Another object of this invention is to provide absorbent alloy fibers of regenerated cellulose containing a uniform dispersion of cyanoethyl cellulose and polyvinylpyrrolidone.

Still another object is the provision of absorbent alloy fibers formed from a mixture of conventional viscose, cyanoethylated viscose, and polyvinylpyrrolidone in which no special drying procedures are required during their manufacture.

These and other objects are accomplished in accordance with the present invention by absorbent alloy fibers, each having a matrix of non-derivatized regenerated cellulose within which regenerated cyanoethyl cellulose and polyvinylpyrrolidone are uniformly dispersed, with the non-derivatized regenerated cellulose being the major portion of the fiber mass.

As employed throughout the description and claims, the terminology "alloy fibers" refers to cellulose fibers having both regenerated cyanoethyl cellulose and polyvinylpyrrolidone contained therein. Similarly "fluid-holding capacity" is a measure of liquid absorbed into the fibers of a mass of alloy fibers together with the liquid retained within the interstices of such fiber mass. The amounts of cyanoethylated viscose and polyvinylpyrrolidone employed in the manufacture of the fibers of the present invention are set forth as percentages based upon the weight of the non-derivatized cellulose in the fibers.

The alloy fibers of the present invention are prepared by mixing a cyanoethylated viscose and an aqueous solution of polyvinylpyrrolidone with a conventional or non-derivatized filament-forming viscose, shaping the mixture into fibers, coagulating and regenerating the shaped fibers and thereafter drying the same. The non-derivatized viscose constitutes the major portion of the mixture and the shaped alloy fibers are coagulated and regenerated by known means, and preferably in an acid bath containing from about 1 to 15 wt. percent sulfuric acid and about 1 to 25 wt. percent sodium sulfate. Zinc sulfate, up to about 10 wt. percent, is often incorporated in the bath as well as other coagulation modifiers, as desired. No special finishes and/or drying procedures are required to render the alloy fibers in a form which can be carded without difficulty.

The non-derivatized viscose which is employed in making the alloy fibers of the present invention is of a composition as is used in making conventional regenerated cellulose fibers. The composition of such viscose is well documented in the prior art and, in general, is produced by reacting alkali cellulose with carbon disulfide, with the resulting sodium cellulose xanthate being diluted with aqueous caustic to provide the resulting viscose with a desired cellulose and alkali content. For example, viscose compositions containing cellulose ranging from 3 to about 12 wt. percent, caustic from about 3 to 12 wt. percent, and carbon disulfide from about 20 to about 60% based upon the weight of cellulose are satisfactory. Additives or modifiers may be mixed in the viscose if desired.

The terminology "cyanoethylated viscose" as used herein refers to a viscose to which acrylonitrile is added or viscose prepared by the simultaneous cyanoethylation and xanthation of alkali cellulose. The latter procedure is preferred from the standpoint of economy and is described in U.S. Pat. Nos. 3,146,116 to A. I. Bates and 3,525,735 to I. K. Miller. Regeneration of such cyanoethylated viscose is accomplished by means of a conventional acidic type coagulating and regenerating bath, as described above. Hydrolysis of the cyanoethyl group on the cellulose during aging and processing produces predominantly carboxyethyl substituent groups on the cellulose in place of the cyanoethyl groups in the resulting regenerated product. The term "regenerated cyanoethyl cellulose" as employed herein refers to a regenerated product as produced by the cyanoethylated viscose described.

Reference to the average degree of substitution (D.S.) of the cyanoethyl cellulose as used herein includes products wherein the anhydroglucose units of the cellulose molecules have an average substitution from about 0.25 to about 0.65 of cyanoethyl groups or chemical groups derived from said cyanoethyl groups by hydrolysis or other chemical change which occurs during manufacture and aging of the material. Thus, the recitation of cyanoethyl cellulose is also meant to include cellulose having carboxyethyl groups and some carboxyamide substituent groups.

To obtain the average degree of substitution prescribed, the amount of acrylonitrile used will vary with the process and conditions employed. Preferably, the simultaneous cyanoethylation and xanthation procedure uses from about 20 to about 50% acrylonitrile based on the weight of the cellulose. Other methods require higher proportions of acrylonitrile to obtain the prescribed degree of substitution.

Polyvinylpyrrolidone which is suitable for use in the present invention has an average molecular weight ranging from about 100,000 to 400,000 and, more desirably, from 160,000 to 360,000 and a preferred K-value of 50–100. The procedure for determining the K-value of such polymers is known in the art, as disclosed in Modern Plastics, 1945, No. 3, starting on Page 157. polyvinylpyrrolidone of desired character is commercially available, for example, under the designations of K-60 and K-90, from General Aniline and Film Corporation.

In making the fibers of the present invention the cyanoethylated viscose and polyvinylpyrrolidone are incorporated into the non-derivatized viscose desirably, but not necessarily, in equal amounts, and preferably in amounts ranging from 10 to 30%, based upon the weight of the cellulose in such viscose. More specifically, the cyanoethylated viscose may be employed in amounts ranging from 5 to 15%, while the polyvinylpyrrolidone is present in amounts ranging from about 5 to 15%. Using less than about 5% of either cyanoethylated viscose of polyvinylpyrrolidone provides fibers which do not differ appreciably from conventional regenerated cellulose fibers in their fluid-holding capacity. Increasing the amount of each of these alloying materials above the range specified generally results in no significant improvement in the fluid-holding capacity of the alloy fibers which are produced.

The polyvinylpyrrolidone described exhibits good solubility in water and, in accordance with the method of the present invention, aqueous solutions of polyvinylpyrrolidone are injected into the non-derivatized viscose as it is pumped to spinnerets for extrusion. The cyanoethylated viscose is also injected into the derivatized viscose during its passage to the spinnerets, either separately of or simultaneously with the introduction of the aqueous solutions of polyvinylpyrrolidone. If it is found necessary to secure a more uniform dispersion, the alloying materials and non-derivatized viscose may be passed through a blender or homogenizer prior to delivery to the extrusion spinnerets.

After the spinning, coagulation and regeneration stages, the shaped continuous tow of filaments undergoes the usual processing which may include stretching, if desired, and is then dried by conventional means. Generally, before drying the continuous tow of filaments is cut into staple of a desired length. Usually, the staple fibers experience no apparent bonding during drying and can be subsequently carded with no difficulty by the manufacture of articles incorporating such fibers.

The alloy fibers of the present invention are adapted for use in a variety of articles, such as sanitary napkins and tampons, in which high fluid retention is an essential characteristic. In the manufacture of such articles, the alloy fibers necessitate no special techniques or equipment and they may be blended with other fibers which may or may not enhance the absorbent properties of the resulting articles. Fibers with which the alloy fibers of the present invention may be blended include, for example, rayon, cotton, chemically modified rayon or cotton, cellulose acetate, nylon, polyester, acrylic, polyolefin, etc.

The fluid-holding capacity of the alloy fibers of the present invention was determined by a procedure, as follows:

Sample staple alloy fibers are carded or otherwise well opened and then conditioned. Two and one half grams of fibers in the form of a carded web about 6 inches long and of variable thickness and width was rolled in the direction of its width to give a 6 inch roll and a string was then looped around the middle of it. The roll was folded around the loop of the string and drawn into a ½ inch tube wherein by means of a plunger and clamp, it was compressed to provide a tampon. After suitable compression the tampon is removed, allowed to stand for a period of time, and was then evaluated by the Syngyna test generally as described by G. W. Rapp in a publication of the Department of Research, Loyola University, Chicago, Illinois, in June 1958.

The following example is provided to further demonstrate the merits of the present invention.

EXAMPLE

A conventional, non-derivatized viscose, an aqueous solution of polyvinylpyrrolidone and a cyanoethylated viscose were prepared separately. The composition of the non-derivatized viscose was 9.0 cellulose, 6.0 sodium hydroxide and 32% carbon disulfide, based on the weight of the cellulose. This viscose had a ball fall of 56 seconds and its common salt test was 7.

The aqueous solution of polyvinylpyrrolidone was prepared simply by dissolving in water polyvinylpyrrolidone, designated as K-60 (General Aniline and Film Corporation) and having an average molecular weight of about 160,000 and K value of 50–62.

Cyanoethylated viscose was prepared by premixing 8.25 lbs. of carbon disulfide and 10.75 lbs. acrylonitrile (34% and 45%, respectively, based on the weight of the cellulose), with the mixture then being charged into an evacuated churn by gravity through a valved stainless steel line. The churn contained a 77 lb. batch of alkali cellulose crumbs and was kept at a temperature of 15° to 32°C during a two hour reaction or churning period. Sufficient water and caustic were added to the churn after the two hour reaction period to provide a viscose of 8.0% cellulose and 6.0% sodium hydroxide (caustic) based on the weight of the viscose, and 34% carbon disulfide and 45% acrylonitrile based upon the weight of the cellulose, after mixing in the churn for an additional one and three quarter hours. The resulting cyanoethylated viscose had a common salt test of 17–21 and a ball fall of 40–50 seconds.

Using conventional spinning equipment, the alloying materials were injected into the non-derivatized viscose as hereafter set forth, with the resulting mixture being extruded through a 720 hole spinneret into an aqueous spinning bath consisting of 7.5% by weight of sulfuric acid, 18% by weight of sodium sulfate, and 3.5% by weight of zinc sulfate. After passage through the spinning bath, the resulting continuous tow was washed with water, desulfurized, and again washed with water. The still wet tow was cut into staple fibers which were, without any further treatment, dried, conditioned and then carded.

The fluid-holding capacity of sample unalloyed fibers and fibers containing the alloying components individually and in combination was determined using the above described test procedure. The compositions of the dry unalloyed and alloyed fibers and the results of the tests performed therein were as follows:

| SAMPLE | %CELLULOSE[1] | %CEC[2] | %POLYVINYL-PYRROLIDONE[3] | FLUID-HOLDING CAPACITIES cc/g. |
| --- | --- | --- | --- | --- |
| A | 100 | 0 | 0 | 3.06; 3.07; 3.14; 3.16 |
| B | 90.9 | 9.1 | 0 | 2.50; 2.55 |
| C | 83.3 | 16.7 | 0 | 2.95; 3.3 |
| D | 71.4 | 28.6 | 0 | 3.35; 3.5 |

| SAMPLE | %CELLULOSE[1] | %CEC[2] | %POLYVINYL-PYRROLIDONE[3] | FLUID-HOLDING CAPACITIES cc/g. |
|---|---|---|---|---|
| | | | -continued | |
| E | 90.9 | 0 | 9.1 | 3.52; 3.53 |
| F | 76.9 | 0 | 23.1 | 4.68; 4.70 |
| G | 80.0 | 10.0 | 10.0 | 5.03; 5.04 |
| H | 74.0 | 13.0 | 13.0 | 5.37; 5.39 |

[1] non-derivatized cellulose
[2] regenerated cyanoethylated cellulose
[3] polyvinylpyrrolidone injected, based on the weight of the cellulose in non-derivatized viscose.

It will be noted that conventional rayon fibers (Sample A), as produced from non-derivatized viscose, exhibit fluid-holding capacities which are less than those of alloy fibers produced from a mixture of conventional viscose and polyvinylpyrrolidone (Samples E and F) and that the fluid-holding capacities of fibers comprised of non-derivatized regenerated cellulose alloyed with regenerated cyanoethyl cellulose increase directly with the regenerated cyanoethyl cellulose content (Samples B, C and D). Significantly, notwithstanding the detrimental effects produced when the lower amounts of cyanoethylated viscose are employed alone as alloying agents, as illustrated by Samples B and C, such derivatized viscose, when combined with polyvinylpyrrolidone, does provide for a synergism, as exhibited by the remarkably improved fluid-holding capacities of the three-component alloy fibers indicated as Samples G and H.

I claim:

1. Fluid absorbent alloy fibers formed from non-derivatized viscose containing at least 5%, based upon the weight of the cellulose in such viscose, of each cyanoethylated viscose and polyvinylpyrrolidone, each of said fibers comprised of a matrix of non-derivatized regenerated cellulose having uniformly dispersed therein regenerated cyanoethyl cellulose having an average degree of cyanoethyl substitution of from about 0.25 to about 0.65 and polyvinylpyrrolidone having an average molecular weight of from about 100,000 to 400,000, the non-derivatized regenerated cellulose being the major portion of the respective fibers, said alloy fibers having fluid holding capacities greater than fibers formed of non-derivatized regenerated cellulose and alloy fibers comprised of a matrix of non-derivatized regenerated cellulose and either of said regenerated cyanoethyl cellulose and said polyvinylpyrrolidone.

2. Fluid absorbent alloy fibers as defined in claim 1 wherein the regenerated cyanoethyl cellulose and polyvinylpyrrolidone are present in generally equal amounts.

3. Fluid absorbent alloy fibers as defined in claim 1 wherein the polyvinylpyrrolidone has an average molecular weight of from about 160,000 to 360,000 and a K-value of from 50 to 100.

4. Fluid absorbent alloy fibers as defined in claim 3 wherein the regenerated cyanoethyl cellulose and polyvinylpyrrolidone are present in generally equal amounts.

* * * * *